(12) United States Patent
Chajut et al.

(10) Patent No.: US 9,950,014 B2
(45) Date of Patent: Apr. 24, 2018

(54) METHODS FOR PREVENTION AND TREATMENT OF PREECLAMPSIA

(71) Applicant: Pluristem Ltd., Haifa (IL)

(72) Inventors: Ayelet Chajut, Ramat Ha'Sharon (IL); Eytan Abraham, Frederick, MD (US)

(73) Assignee: PLURISTEM LTD., Haifa (IL)

( * ) Notice: Subject to any disclaimer, the term of this patent is extended or adjusted under 35 U.S.C. 154(b) by 131 days.

(21) Appl. No.: 14/425,960

(22) PCT Filed: Aug. 31, 2013

(86) PCT No.: PCT/IB2013/058186
§ 371 (c)(1),
(2) Date: Mar. 4, 2015

(87) PCT Pub. No.: WO2014/037863
PCT Pub. Date: Mar. 13, 2014

(65) Prior Publication Data
US 2015/0216907 A1 Aug. 6, 2015

Related U.S. Application Data

(60) Provisional application No. 61/825,037, filed on May 19, 2013, provisional application No. 61/815,760, filed on Apr. 25, 2013, provisional application No. 61/696,442, filed on Sep. 4, 2012.

(51) Int. Cl.
*A61K 35/50* (2015.01)
*A61K 35/28* (2015.01)
*A61K 35/35* (2015.01)
*C12N 5/073* (2010.01)
*C12N 5/077* (2010.01)

(52) U.S. Cl.
CPC ............. *A61K 35/35* (2013.01); *A61K 35/28* (2013.01); *A61K 35/50* (2013.01); *C12N 5/0605* (2013.01); *C12N 5/0653* (2013.01); *C12N 2513/00* (2013.01)

(58) Field of Classification Search
None
See application file for complete search history.

(56) References Cited

U.S. PATENT DOCUMENTS

| | | |
|---|---|---|
| 6,911,201 B1 | 6/2005 | Merchav et al. |
| 7,534,609 B2 | 5/2009 | Merchav et al. |
| 7,678,573 B2 | 3/2010 | Merchav et al. |
| 8,481,488 B2 * | 7/2013 | Carter .................. A61K 31/675 424/85.1 |
| 8,524,496 B2 | 9/2013 | Meiron et al. |
| 8,529,888 B2 | 9/2013 | Meiron et al. |
| 9,096,827 B2 | 8/2015 | Meiron et al. |
| 9,393,273 B2 | 7/2016 | Meiron |
| 9,512,393 B2 | 12/2016 | Kasuto et al. |
| 2005/0176143 A1 | 8/2005 | Merchav et al. |
| 2005/0181504 A1 | 8/2005 | Merchav et al. |
| 2009/0004738 A1 | 1/2009 | Merchav et al. |
| 2010/0035297 A1 * | 2/2010 | Traktuev ............ G01N 33/5044 435/29 |
| 2010/0124569 A1 * | 5/2010 | Abbot .................... A61K 35/50 424/484 |
| 2010/0209403 A1 | 8/2010 | Meiron et al. |
| 2011/0129447 A1 | 6/2011 | Meretski et al. |
| 2011/0129486 A1 | 6/2011 | Meiron |
| 2011/0171182 A1 | 7/2011 | Meiron et al. |
| 2011/0256108 A1 | 10/2011 | Meiron et al. |
| 2011/0256159 A1 | 10/2011 | Meiron et al. |
| 2011/0256160 A1 | 10/2011 | Meiron et al. |
| 2011/0293583 A1 | 12/2011 | Aberman |
| 2012/0122220 A1 | 5/2012 | Perski et al. |
| 2012/0164114 A1 * | 6/2012 | Abbot .................... A61K 35/50 424/93.7 |
| 2013/0004465 A1 | 1/2013 | Aberman |
| 2013/0039892 A1 | 2/2013 | Aberman |
| 2013/0259843 A1 | 10/2013 | Duda et al. |
| 2013/0323213 A1 | 12/2013 | Meiron et al. |
| 2013/0337558 A1 | 12/2013 | Meiron et al. |
| 2014/0017209 A1 | 1/2014 | Aberman et al. |
| 2014/0030805 A1 | 1/2014 | Kasuto et al. |
| 2014/0242039 A1 | 8/2014 | Meiron et al. |
| 2015/0017122 A1 * | 1/2015 | Rolfo .................... A61K 38/19 424/85.2 |
| 2015/0125138 A1 | 5/2015 | Duda et al. |
| 2015/0232797 A1 | 8/2015 | Kasuto et al. |
| 2016/0022738 A1 | 1/2016 | Meretski et al. |
| 2016/0058799 A1 | 3/2016 | Aberman |
| 2016/0186259 A1 | 6/2016 | Ofir et al. |
| 2016/0271184 A1 | 9/2016 | Meiron |

FOREIGN PATENT DOCUMENTS

| | | |
|---|---|---|
| RU | 22718174 C1 | 3/2006 |
| WO | WO 2007/108003 A2 | 9/2007 |
| WO | WO 2009/037690 A1 | 3/2009 |
| WO | WO 2011/044251 A1 | 4/2011 |
| WO | WO 2013/093878 A1 | 6/2013 |

OTHER PUBLICATIONS

Redman et al, "Latest Advances in understanding preeclampsia" Science, 2005, vol. 308, pp. 1592-1594.*
Zhou et al, "Angiotensin receptor agonistic autoantibodies induce pre-eclampsia in pregnant mice" Nature Medicine, 2008, vol. 14, No. 8, pp. 855-862.*

(Continued)

*Primary Examiner* — Allison M Fox
(74) *Attorney, Agent, or Firm* — Lando & Anastasi, LLP

(57) ABSTRACT

Methods for treating or preventing preeclampsia or eclampsia by administering adherent stromal cells are described. The adherent stromal cells may be derived from bone marrow, placenta, or adipose tissue. Also described is the use of adherent stromal cells for the manufacture of a medicament, and an article of manufacture comprising a packaging material which comprises a label for use in treating or preventing preeclampsia or eclampsia.

20 Claims, 7 Drawing Sheets

(56) References Cited

OTHER PUBLICATIONS

George et al "Mechanisms and Potential Therapies for Preeclampsia" Curr Hypertens Rep, 2011, vol. 13, pp. 269-275.*
Kranz et al., Transplantation of placenta-derived mesenchymal stromal cells upon experimental stroke in rats. Brain Res. Feb. 22, 2010;1315:128-36. doi: 10.1016/j.brainres.2009.12.001. Epub Jan. 12, 2010.
Sane et al., Bone marrow stem cell therapy in hypertensive disorders of pregnancy improves placental circulation, maternal and fetal outcome. J Develop Origins Health Dis. Sep. 2011;2:S80. PII-164 Abstract.
George, Eric M., and Joey P. Granger. "Mechanisms and potential therapies for preeclampsia." Current hypertension reports 13.4 (2011): 269-275.
George, Eric M., and Joey P. Granger. "Recent insights into the pathophysiology of preeclampsia." Expert Rev Obstet Gynecol. 5.5 (2010): 557-566.

* cited by examiner

METHODS FOR PREVENTION AND TREATMENT OF PREECLAMPSIA

CROSS-REFERENCE TO RELATED APPLICATIONS

This application is a national stage filing under U.S.C. § 371 of PCT International Application PCT/IB2013/058186, entitled "METHODS FOR PREVENTION AND TREATMENT OF PREECLAMPSIA" with an international filing date of Aug. 31, 2013, which claims priority under 35 U.S.C. § 119(e) to U.S. Provisional Application Ser. No. 61/825,037, filed on May 19, 2013, and U.S. Provisional Application Ser. No. 61/815,760, filed on Apr. 25, 2013, and U.S. Provisional Application Ser. No. 61/696,442, filed on Sep. 4, 2012, which are herein incorporated by reference in their entirety.

PREECLAMPSIA DISEASE

Preeclampsia (gestational proteinuric hypertension; PE) appears in three to five percent of all pregnancies. [1] It is the second most common cause of pregnancy-related maternal death in the USA and is a leading cause of maternal mortality in developing countries. PE accounts for approximately 15% of all maternal deaths worldwide, translating to an estimated 60,000 maternal deaths per year, i.e. a woman dies every ten minutes from complications of preeclampsia [1, 2].

PE is a systemic syndrome presenting clinically with hypertension, edema and proteinuria during pregnancy. It is diagnosed by the combined detection of two factors: new-onset hypertension (sustained sitting blood pressure [BP]≥140/90 mm Hg) and proteinuria (≥300 mg/24 h). The only current effective treatment for PE is delivery. Complications of PE include convulsions, hypercoagulability, acute renal failure and pulmonary edema [1, 3].

During normal human pregnancy, blood flow to the uterus increases, reaching up to approximately 25% of the cardiac output by late pregnancy. Modulation and dilation of the spiral arteries during the first trimester reduces uteroplacental vascular resistance and increases uteroplacental blood flow. In women that develop preeclampsia, uteroplacental blood flow is reduced by 50% to 70% [3, 4].

The mother's health depends primarily on the type of preeclampsia (mild or severe), prevention of complications (such as seizures), and timely delivery.

The perinatal outcome depends on the severity of the condition and therefore the ability to bring the pregnancy to term. In cases of severe preeclampsia, early delivery which results in fetal death is the outcome in many cases.

Preeclampsia is characterized by a generalized systemic maternal inflammatory response [8], although normal pregnancy itself is a state of systemic inflammation. The systemic inflammatory response in normal pregnancy is not intrinsically different from that of preeclampsia, but is just milder. This finding led to the proposal that preeclampsia develops when the systemic inflammatory process reaches the extreme end of a range of maternal systemic inflammatory responses engendered by pregnancy itself, causing one or another maternal systems to decompensate [8]. According to this theory, the inflammatory response generates oxidative stress and, conversely, oxidative stress can stimulate an inflammatory response, forming the foundation for a positive feedback system. One or more pro-inflammatory factors released from the syncytial surface of the placenta into the maternal circulation may be involved in this scenario.

Preeclampsia is a multisystem disorder specific to human pregnancy; the basis for its development is established early in pregnancy. The pathologic hallmark appears to be abnormal trophoblast implantation from 16 to 20 weeks of gestation and therefore abnormal physiological alteration in the maternal vessels which are required for adequate perfusion of the placental bed. As pregnancy progresses, the metabolic demands of the fetoplacental unit increase, and due to the abnormally shallow invasion of the placenta, the spiral arterioles do not dilate sufficiently to accommodate the required increase in blood flow. This results in placental dysfunction and the abnormal release of factors from the ischemic placenta that leads to vasospasm and endothelial injury. Recent studies suggest that an imbalance in pro-angiogenic (e.g., VEGF and placental growth factor [PlGF]) and anti-angiogenic factors (e.g., sFlt1 [a soluble VEGF receptor], and endoglin [a soluble TGF-β receptor]) in the maternal, fetal, and placental circulation is involved in the development of PE. Imbalance between circulating pro- and anti-angiogenic factors results in further abnormal development of placental vasculature and reduction in circulating factors which are important for vascular health and vasodilation such as NO and $PGI_2$.

While the molecular mechanisms underlying preeclampsia are poorly understood, research has suggested a link between inadequate fetal tolerance towards feto-paternal antigens during conception and implantation [1, 3, 5-7]. Interestingly, a link between the level of microchimerisms (circulating cells in the mother that are remnants from the maternal grandmother or previous pregnancies) and the occurrence of PE has been established, wherein higher levels of microchimerisms reduce the chances of PE. This suggests that cells from the fetoplacental interface, which are similar in origin to adherent cells from bone marrow, placenta, and adipose tissues (See, e.g., cells described in International Patent Publication Numbers WO 2007/108003 and WO 2009/037690, incorporated herein by reference in their entireties) may reduce the occurrence of PE [8].

In most cases, preeclampsia and eclampsia disappear within one to two weeks of delivery, although 20% of woman develop hypertension and microalbuminuria within seven years and there is a two-fold increase in long term risk of vascular disease of the heart and brain [1, 3].

Limitations of Current Treatment Options

Despite progress in PE research, there remains no treatment for preeclampsia other than delivery of the fetus. The use of anti-hypertensive drugs does not usually alleviate PE symptoms. Management of preeclampsia depends on gestational age and severity of the disease. However, in all cases, delivery is the only treatment of choice. Patients with mild PE can be managed expectantly. In some cases, PE can be stabilized temporarily by intravenous delivery of magnesium sulfate to forestall seizures while steroid injections are administered to promote fetal lung maturation in view of delivery. In these cases, an in-hospital stay is required and fetal status is closely monitored. However, in cases of more severe PE, or eclampsia, where there is organ dysfunction, fetal compromise, or HELLP syndrome (elevated liver enzymes, decrease platelet count, and hemolysis), immediate delivery is suggested regardless of gestational age [1, 3, 9, 10].

PE Animal Models

Available models of human preeclampsia include:

Clamping the abdominal aorta or occlusion and/or banding of the arteries supplying the uterus which result in a significant (approximately 50%) reduction of uteroplacental perfusion pressure in several species, thus imitating preeclampsia [11].

Inbred BPH-5 mice, derived from brother-sister mating of borderline hypertensive BPH/2 mice, exhibit increases in blood pressure in late gestation (from 130 to 160 mmHg, compared with 105 mmHg in control C57BL-6) that resolve within 2 days of delivery and are accompanied by increases in proteinuria. Exogenous VEGF and antioxidants decrease blood pressure and increase fetal survival [7, 12].

The SHHF/Mcc-fa(cp) (spontaneous hypertension and heart failure) rat exhibits spontaneous pregnancy-associated hypertension, small-for-gestational-age offspring, and altered placental gene expression [13].

Genetically modified mouse models for PE, including: mice with a genetic knockout of p57Kip2, a potent inhibitor of several cyclin/cyclin-dependent kinase complexes; eNOS-deficient mice; and mice deficient in Catechol-O-methyltransferase (COMT), which is a rate-limiting enzyme in estrogen catabolization [14].

Cell Therapy Mechanisms of Action

The etiology of PE includes abnormal modulation of the vasculature as well as an anomalous systemic profile of angiogenesis-related cytokines, primarily the elevation of anti-angiogenic proteins.

Three dimensionally-adherent cells from bone marrow, placenta, and adipose tissues (See, e.g., International Patent Publication Numbers WO 2007/108003 and WO 2009/037690 [3D-adherent cells by Plurix; PLX cells]) secrete high levels of pro-angiogenic factors, including, for example, VEGF, angiogenin, PDGF, and IL-8, as well as tissue modulating factors such as TIMPs and MMPs. In vitro, media that is conditioned by adherent placental or adipose tissue cells is capable of increasing both endothelial cell and smooth muscle cell proliferation, which are two processes that are central to angiogenesis and vascular modulation. In addition, the adherent cells exhibit significant immunomodulatory properties.

Experiments in animal models as well as clinical trials show that adherent placental or adipose tissue cell administration (IM) in the hind limb ischemia model and in patients suffering from peripheral arterial disease (PAD) results in increased perfusion and angiogenesis, which is manifested by the de-novo formation of capillaries and, most likely, remodeling of existing vasculature to increase blood flow (vasculogenesis).

Accordingly, aspects of the invention relate to the capability of adherent placental or adipose tissue cell therapy to prevent or treat preeclampsia.

One embodiment is directed to a method of treating or preventing preeclampsia or eclampsia in a subject in need thereof, the method comprising administering to said subject a therapeutically or prophylactically effective amount of adherent stromal cells, thereby treating or preventing the preeclampsia or eclampsia. In certain embodiments, the cells are obtained from bone marrow, placenta, or adipose tissue.

Another embodiment is directed to the use of adherent stromal cells for the manufacture of a medicament for treating or preventing preeclampsia or eclampsia. In certain embodiments, the cells are obtained from bone marrow, placenta, or adipose tissue.

Certain embodiments are directed to adherent stromal cells for use in the treatment or prevention of preeclampsia or eclampsia. In one embodiment, the cells are obtained from bone marrow, placenta, or adipose tissue.

Another embodiment is directed to an article of manufacture comprising a packaging material which comprises a label for use in treating or preventing preeclampsia or eclampsia, said packaging material packaging a pharmaceutically effective amount of adherent stromal cells. In one embodiment, the cells are obtained from bone marrow, placenta, or adipose tissue.

In certain embodiments of the method, use, adherent stromal cells, or article of manufacture the subject has early-onset preeclampsia. In other embodiments the subject is at a period of gestation of from about 20 weeks to about 34 weeks. In still other embodiments the subject has late-onset preeclampsia. In additional embodiments the subject is at a period of gestation of from about 34 weeks to about 38 weeks or more.

In some embodiments, the subject has an increased inflammatory response to pregnancy. In other embodiments, the subject has one or more risk factors for preeclampsia selected from preeclampsia in a first-degree relative, preeclampsia history in a prior pregnancy, reduced serum concentration of placental growth factor (PlGF), an increased serum concentration of soluble fms-like tyrosine kinase-1 (sFlt-1), an increased serum concentration of soluble endoglin, a risk factor for a cardiovascular disease, pre-existing sub-clinical endothelial dysfunction, chronic hypertension, diabetes mellitus, hyperlipidemia, maternal obesity, insulin resistance, high blood pressure in early pregnancy, renal disease, metabolic syndrome, a hypercoagulable state, young maternal age, advanced maternal age, poor placentation, increased placental mass, multifetal gestation, a hydatidiform mole, and prenatal paternity by a man who fathered a prior preclamptic pregnancy with a prior partner.

In other embodiments, the preeclampsia or eclampsia is prevented by administering the adherent stromal cells prior to gestation. In still further embodiments, the preeclampsia or eclampsia is prevented by administering the adherent stromal cells at any time during gestation. On other embodiments, the preeclampsia or eclampsia is prevented by administering the stromal cells at a period of gestation of from about 16 weeks to about 20 weeks.

In some embodiments, the adherent stromal cells are administered systemically, while in others the adherent cells are administered locally. In other embodiments, the adherent cells are administered intramuscularly. In certain embodiments, the adherent cells are administered subcutaneously.

In some embodiments, the adherent cells comprise a positive marker expression selected from the group consisting of CD73, CD90, CD29 and CD105. In other embodiments, the adherent cells comprise a negative marker expression selected from the group consisting of CD3, CD4, CD45, CD80, HLA-DR, CD11b, CD14, CD19, CD34 and CD79.

In some embodiments, the adherent stromal cells are obtained from a three-dimensional (3D) culture. In particular embodiments, the three-dimensional (3D) culture comprises a 3D bioreactor. In still other embodiments, culturing of the adherent cells in the 3D culture is effected under perfusion. In additional embodiments, culturing of the adherent cells is effected for at least 3 days. While in some embodiments, culturing of the adherent cells is effected until at least 10% of the adherent cells are proliferating.

In some embodiments, the adherent cells comprise cells cultured from the placenta or adipose tissue under 2 dimensional (2D) culturing conditions.

In some embodiments, the adherent stromal cells are autologous to the mother or fetus. In other embodiments, the adherent stromal cells are allogeneic to the mother and/or fetus.

Further objects and advantages of the invention will be set forth in part in the description which follows, and in part will be obvious from the description, or may be learned by practice of the invention.

DESCRIPTION OF CERTAIN EMBODIMENTS

Figure 1:
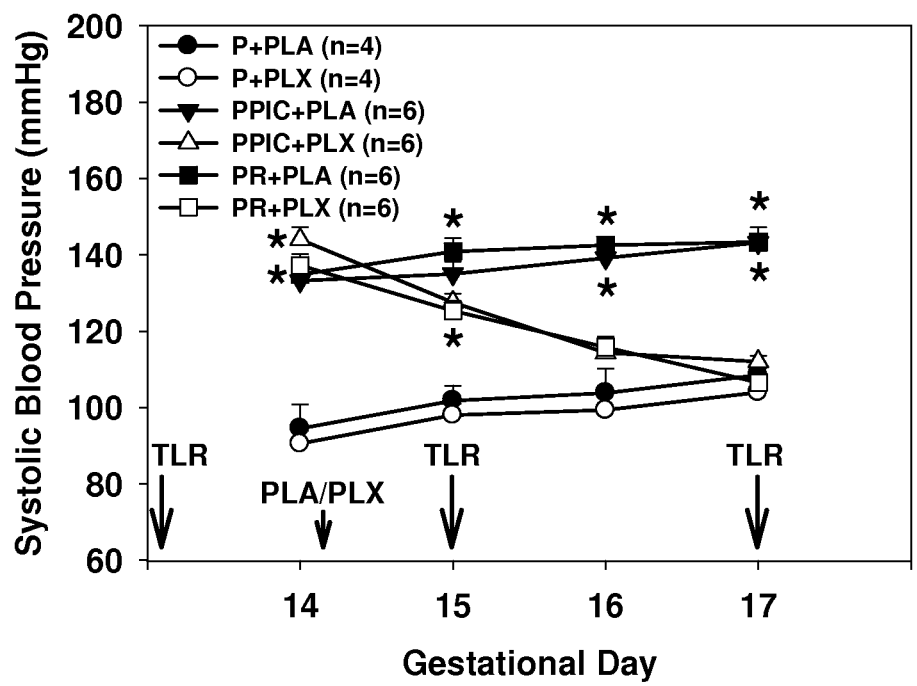
FIG. 1. P (pregnant), PPIC (pregnant+poly I:C (TLR3 agonist)), and PR (pregnant+R837 (TLR7 agonist)) mice were treated with either PLA vehicle or PLX cells ($10^6$ cells total) administered by i.m. injections in the right leg on gestational day 14 following systolic blood pressure ("SBP") measures. SBP progressively decreased during pregnancy returning to basal levels by day 17. N is provided in parentheses. Data are presented as mean+/−SEM. *$p<0.05$ vs. P+PLA.

The principles and operation of the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Embodiments of the invention relate to methods of treating or preventing preeclampsia or pregnancy induced hypertension or eclampsia in a subject in need thereof, wherein the methods include administering to the subject a therapeutically or prophylactically effective amount of adherent stromal cells. "Adherent stromal cells" are stromal cells which can be isolated and/or maintained by adherence to an adherent material, e.g., plastic, in standard culture conditions. That is, "adherent stromal cells" refers to a homogeneous or heterogeneous population of cells which are anchorage dependent in vitro, i.e., which require attachment to a surface or to other cells in order to grow in vitro. Adherent stromal cells may comprise at least one 'stromal cell phenotype." As used herein "a stromal cell phenotype" refers to a structural or functional phenotype typical of a bone-marrow derived stromal (i.e., mesenchymal) cell. Thus, for example, the cells may have a spindle shape. Alternatively, or additionally, the cells may express a marker or a collection of markers (e.g. surface marker) typical to stromal cells.

Adherent stromal cells may be derived from a placenta or adipose or bone marrow tissue or any other source for adherent stromal cells. Embodiments further relate to articles of manufacture including a packaging material including a label for use in treating or preventing preeclampsia or pregnancy induced hypertension or eclampsia, wherein the packaging material packages a pharmaceutically effective amount of adherent stromal cells from a placenta or adipose tissue. In some embodiments, the adherent stromal cells are adherent stromal cells from placenta or adipose tissue, described in International Patent Publication Numbers WO 2007/108003 and WO 2009/037690 (3D- adherent cells by Plurix; PLX cells), each of which is incorporated herein by reference herein in its entirety.

Aspects of the invention further relate to a multifold mode of action for preeclampsia or pregnancy induced hypertension or eclampsia treatment or prophylaxis using adherent stromal cells such as from placenta or adipose tissue, including, for example, PLX cells. In some embodiments, preeclampsia is prevented by administering adherent stromal cells prior to gestation. In other embodiments, preeclampsia is prevented by administering adherent stromal cells at any time during gestation. In some embodiments, adherent stromal cell therapy causes a shift in circulating angiogenic cytokines from an anti-angiogenic profile to a pro-angiogenic profile, thereby inducing an endocrine angiogenesis effect at the uteroplacental interface. In some embodiments, this cell therapy induces modulation of the spiral arterioles at the uteroplacental interface, causing vascular modulation and vasodilation and increased blood flow. In certain embodiments, the cell therapy induces systemic suppression of inflammatory and immune processes which may be involved in PE.

In some embodiments, in cases of early and severe-onset preeclampsia (including subjects at a gestation period of between about 20 to about 24 weeks) in which fetal survival chances are low and maternal health is compromised, intramuscular administration of adherent stromal cells reverses or alleviates PE symptoms and improves the prognosis of both mother and child.

Placenta or adipose tissue derived adherent cells can be propagated using two dimensional or three dimensional culturing conditions. As used herein the phrase "three dimensional culture" refers to a culture in which the cells are disposed to conditions which are compatible with cell growth while allowing the cells to grow in more than one layer. It is well appreciated that the in situ environment of a cell in a living organism (or a tissue) is in a three dimensional architecture. Cells are surrounded by other cells. They are held in a complex network of extra cellular matrix nanoscale fibers that allows the establishment of various local microenvironments. Their extra cellular ligands mediate not only the attachment to the basal membrane but also access to a variety of vascular and lymphatic vessels. Oxygen, hormones and nutrients are ferried to cells and waste products are carried away. The conditions in the three dimensional culture of the invention are designed to mimic such an environment as is further exemplified below.

It will be appreciated that the conditions of the three-dimensional culture are such that enable expansion of the adherent cells. As used herein the terms "expanding" and "expansion" refer to substantially differentiation-less maintenance of the cells and ultimately cell growth, i.e., increase of a cell population (e.g., at least 2 fold) without differentiation accompanying such increase.

As used herein the terms "maintaining" and "maintenance" refer to substantially differentiation-less cell renewal, i.e., substantially stationary cell population without differentiation accompanying such stationarity.

As mentioned, the adherent cells of this specific aspect of the invention are retrieved from an adipose or placental tissue.

Placental cells may be obtained from a full-term or pre-term placenta. Placenta is preferably collected once it has been ex blooded. The placenta is preferably perfused for a period of time sufficient to remove residual cells. The term "perfuse" or "perfusion" used herein refers to the act of pouring or passing a fluid over or through an organ or tissue. The placental tissue may be from any mammal; for example, the placental tissue is human. A convenient source of placental tissue is from a post partum placenta (e.g., 1-6 hours), however, the source of placental tissue or cells or the method of isolation of placental tissue is not critical to the invention.

Placenta derived adherent cells may be obtained from both fetal (i.e., amnion, chorion, chorionic villi or inner parts of the placenta and maternal (i.e., decidua basalis, and decidua parietalis) parts of the placenta. Tissue specimens are washed in a physiological buffer [e.g., phosphate-buffered saline (PBS) or Hank's buffer]. Single-cell suspensions are made by treating the tissue with a digestive enzyme (see below) or/and mincing and flushing the tissue parts through a nylon filter or by gentle pipetting (Falcon, Becton, Dickinson, San Jose, Calif.) with washing medium.

Adipose tissue derived adherent cells may be isolated by a variety of methods known to those skilled in the art. For example, such methods are described in U.S. Pat. No. 6,153,432. The adipose tissue may be derived from omental/visceral, mammary, gonadal, or other adipose tissue sites. One source of adipose tissue is omental adipose. In humans, the adipose is typically isolated by liposuction.

Isolated adherent cells from adipose tissue may be derived by treating the tissue with a digestive enzyme such as collagenase, trypsin and/or dispase; and/or effective concentrations of hyaluronidase or DNAse; and ethylenediaminetetra-acetic acid (EDTA); at temperatures between 25-50° C., for periods of between 10 minutes to 3 hours. The cells may then be passed through a nylon or cheesecloth mesh filter of between 20 microns to 1 mm. The cells are then subjected to differential centrifugation directly in media or over a Ficoll or Percoll or other particulate gradient. Cells are centrifuged at speeds of between 100 to 3000×g for periods of between 1 minutes to 1 hour at temperatures of between 4-50° C. (see U.S. Pat. No. 7,078,230).

Regardless of the origin (e.g., placenta or adipose tissue), cell retrieval is preferably effected under sterile conditions. Once isolated cells are obtained, they are allowed to adhere to an adherent material (e.g., configured as a surface) to thereby isolate adherent cells. Culturing may proceed under 2D conditions and cells may be further transferred to 3D conditions.

As used herein "an adherent material" refers to a synthetic, naturally occurring or a combination of same of a non-cytotoxic (i.e., biologically compatible) material having a chemical structure (e.g., charged surface exposed groups) which may retain the cells on a surface. Examples of adherent materials which may be used in accordance with the invention include, but are not limited to, a polyester, a polypropylene, a polyalkylene, a polyfluorochloroethylene, a polyvinyl chloride, a polystyrene, a polysulfone, a cellulose acetate, a glass fiber, a ceramic particle, a matrigel, an extra cellular matrix component (e.g., fibronectin, chondronectin, laminin), a collagen, a poly L lactic acid and an inert metal fiber.

Further steps of purification or enrichment for adherent stromal cells may be effected using methods which are well known in the art (such as by FACS using adherent stromal cell marker expression, as further described herein below).

Non-limiting examples of base media useful in culturing according to the invention include Minimum Essential Medium Eagle, ADC-I, LPM (Bovine Serum Albumin-free), F 10 (HAM), F 12 (HAM), DCCM 1, DCCM2, RPMI 1640, BGJ Medium (with and without Fitton-Jackson Modification), Basal Medium Eagle (BME—with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5 A Medium, Medium M 199 (M199E—with Earle's sale base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. A preferred medium for use in the invention is DMEM. These and other useful media are available from GIBCO, Grand Island, N.Y., USA and Biological Industries, Bet HaEmek, Israel, among others. A number of these media are summarized in Methods in Enzymology, Volume LVIII, "Cell Culture", pp. 62 72, edited by William B. Jakoby and Ira H. Pastan, published by Academic Press, Inc.

The medium may be supplemented such as with serum such as fetal serum of bovine or other species, and optionally or alternatively, growth factors, vitamins (e.g. ascorbic acid), cytokines, salts (e.g. B-glycerophosphate), steroids (e.g. dexamethasone) and hormones e.g., growth hormone, erythropoietin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor, fibroblast growth factor, nerve growth factor, cilary neurotrophic factor, platelet derived growth factor, and bone morphogenetic protein at concentrations of between picogram/ml to milligram/ml levels.

It is further recognized that additional components may be added to the culture medium. Such components may be antibiotics, antimycotics, albumin, amino acids, and other components known to the art for the culture of cells. Additionally, components may be added to enhance the differentiation process when needed (see further below).

It will be appreciated that in case the adherent stromal cells of the invention are administered to a human subject, the cells and the culture medium (e.g., with the above described medium additives) should be substantially xeno-free, i.e., devoid of any animal contaminants e.g., mycoplasma. For example, the culture medium can be supplemented with a serum-replacement, human serum and/or synthetic or recombinantly produced factors so that the cells may be grown in under serum-free conditions.

As mentioned, once adherent cells are at hand they may be passaged to two dimensional or three dimensional settings. It will be appreciated though, that the cells may be transferred to a 3D-configured matrix immediately after isolation or alternatively, may be passaged to three dimensional settings following two dimensional conditions.

For high scale production, culturing can be effected in a 3D bioreactor. Configuring an adherent substrate for 3D culturing thereby providing a growth matrix that substantially increases the available attachment surface for the adherence of the cells so as to mimic the infrastructure of the tissue (e.g., placenta).

Examples of such bioreactors include, but are not limited to, a plug flow bioreactor, a continuous stirred tank bioreactor, a stationary-bed bioreactor, a CelliGen Plus® bioreactor system (New Brunswick Scientific (NBS) or a BIOFLO 310 bioreactor system (New Brunswick Scientific (NBS). For example, the Celligen bioreactor is capable of 3D expansion of adherent cells under controlled conditions (e.g. pH, temperature and oxygen levels) and with constant cell growth medium perfusion. Furthermore, the cell cultures can be directly monitored for concentration levels of glucose, lactate, glutamine, glutamate and ammonium. The glucose consumption rate and the lactate formation rate of the adherent cells enable to measure cell growth rate and to determine the harvest time.

Other 3D bioreactors that can be used with the invention include, but are not limited to, a continuous stirred tank bioreactor, where a culture medium is continuously fed into the bioreactor and a product is continuously drawn out, to maintain a time-constant steady state within the reactor. A stirred tank bioreactor with a fibrous bed basket is available for example at New Brunswick Scientific Co., Edison, N.J.), A stationary-bed bioreactor, an air-lift bioreactor, where air is typically fed into the bottom of a central draught tube flowing up while forming bubbles, and disengaging exhaust gas at the top of the column], a cell seeding perfusion bioreactor with Polyactive foams [as described in Wendt, D. et al., Biotechnol Bioeng 84: 205-214, (2003)] tubular poly-L-lactic acid (PLLA) porous scaffolds in a Radial-flow perfusion bioreactor [as described in Kitagawa et al., Biotechnology and Bioengineering 93(5): 947-954 (2006). Other bioreactors which can be used in accordance with the invention are described in U.S. Pat. Nos. 6,277,151, 6,197, 575, 6,139,578, 6,132,463, 5,902,741 and 5,629,186.

Cell seeding is preferably effected 100,000-1,500,000 cells/mm at seeding. In an exemplary embodiment a total of $150\pm30\times10^6$ cells are seeded, $3\text{-}5\times10^6$ cell/gr carrier are seeded, or $0.015\text{-}0.1\times10^6$ cell/ml are seeded.

Cells can be harvested when at least about 10% of cells are proliferating while avoiding uncontrolled differentiation and senescence.

Culturing is effected for at least about 2 days, 3 days, 4 days, 5 days, 10 days, 20 days, a month or even more. It will be appreciated that culturing in a bioreactor may prolong this period. Culturing of the adherent cells in the 3D culture can be effected under a continuous flow of a culture medium. Passaging may also be effected to increase cell number. It will be appreciated that culture medium may be changed in order to prolong and improve culturing conditions.

Adherent cells of some embodiments of the present invention comprise at least about 10%, 28%, 30%, 50%, 80% or more proliferative cells (as can be assayed by FACS monitoring S and G2/M phases). Alternatively or additionally, the cells may express a marker or a collection of markers (e.g. surface marker) typical to adherent stromal cells. Examples of such cell surface markers (positive and negative) include but are not limited to CD 105+, CD29+, CD44+, CD73+, CD90+, CD3−, CD4−, CD34−, CD45−, CD80−, CD19−, CD5−, CD20−, CD11b−, CD14−, CD 19−, CD79−, HLA-DR−, and FMC7−. Other adherent stromal cell markers include but are not limited to tyrosine hydroxylase, nestin and H-NF.

Populations of cells generated according to the present teachings are characterized by a unique protein expression profile. Thus for example, adherent stromal cells of placenta or adipose tissue are capable of expressing and/or secreting high levels of selected factors. For example, such cells express or secrete SCF, Flt-3, H2A histone family (H2AF) or Aldehyde dehydrogenase X (ALDH X) at least 2, 3, 4, 5, 6, 7, 8, 9, 10, 11 or even 12 fold higher than that expressed or secreted by adherent cells of placenta or adipose tissue grown in a 2D culture. Additionally or alternatively, population of cells of the invention secrete or express IL-6, eukaryotic translation elongation factor 2 (EEEF2), reticulocalbin 3, EF-hand calcium binding domain (RCN2) or calponin 1 basic smooth muscle (CNN1) at a level least 2, 3 or 5 fold higher than that expressed or secreted by adherent cells of placenta or adipose tissue grown in a 2D culture. Additionally or alternatively, population of cells of the invention are characterized by lower level of expression of various other proteins as compared to 2D cultured cells. Thus for example, secrete or express less than 0.6, 0.5, 0.25 or 0.125 of the expression level of heterogeneous nuclear ribonucleoprotein H1 (Hnrph1), CD44 antigen isoform 2 precursor, 3 phosphoadenosine 5 phosphosulfate synthase 2 isoform a (Papss2) or ribosomal protein L7a (rpL7a) expressed or secreted by adherent cells of placenta or adipose tissue grown in a 2D culture.

The subject receiving treatment may be any pregnant mammal in need of treatment or prophylaxis for preeclampsia or eclampsia including, e.g., human or domesticated animals including, but not limited to, horses (i.e. equine), cattle, goat, sheep, pig, dog, cat, camel, alpaca, llama and yak.

Mode of Administration

In some embodiments, adherent stromal cells are administered locally. In further embodiments, the cells are administered systemically.

In some embodiments, the cells are administered locally via intramuscular or subcutaneous injection. Intramuscular (IM) administration is proven safe in a clinical trial for critical limb ischemia (CLI). Local administration also facilitates improvement of symptoms of hind limb ischemia (HLI) when IM injection is remote to the injury (non-ligated leg). IM administration also allows secretion of cytokines at systemically detectable levels, and offers ease and speed of delivery.

In some embodiments, the adherent stromal cells are autologous to the mother or fetus. In other embodiments, the adherent stromal cells are allogeneic to the mother and/or fetus.

In any of the methods described herein, the cells can be administered either per se or, preferably as a part of a pharmaceutical composition that further comprises a pharmaceutically acceptable carrier. As used herein a "pharmaceutical composition" refers to a preparation of the adherent cells of the invention (i.e., adherent cells of a tissue selected from the group consisting of placenta and adipose tissue, which are obtained from a three-dimensional culture), with other chemical components such as pharmaceutically suitable carriers and excipients. The purpose of a pharmaceutical composition is to facilitate administration of the cells to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

According to a preferred embodiment of the invention, the pharmaceutical carrier is an aqueous solution of saline.

Techniques for formulation and administration of drugs may be found in "Remington's Pharmaceutical Sciences," Mack Publishing Co., Easton, Pa., latest edition, which is incorporated herein by reference.

One may administer the pharmaceutical composition in a systemic manner. Alternatively, one may administer the pharmaceutical composition locally, for example, via injection of the pharmaceutical composition directly into a tissue region of a patient.

Pharmaceutical compositions of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, physiological salt buffer, or freezing medium containing cryopreservents. For transmucosal administration, penetrants appropriate to the barrier to be permeated are used in the formulation. Such penetrants are generally known in the art.

For any preparation used in the methods of the invention, the therapeutically effective amount or dose can be estimated initially from in vitro and cell culture assays. Preferably, a dose is formulated in an animal model to achieve a desired concentration or titer. Such information can be used to more accurately determine useful doses in humans. Toxicity and therapeutic efficacy of the active ingredients described herein can be determined by standard pharmaceutical procedures in vitro, in cell cultures or experimental animals.

The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition, (see e.g., Fingl, et ai, 1975, in "The Pharmacological Basis of Therapeutics", Ch. 1 p. 1). For example, Parkinson's patient can be monitored symptomatically for improved motor functions indicating positive response to treatment.

For injection, the active ingredients of the pharmaceutical composition may be formulated in aqueous solutions, preferably in physiologically compatible buffers such as Hank's solution, Ringer's solution, or physiological salt buffer.

Dosage amount and interval may be adjusted individually to levels of the active ingredient which are sufficient to effectively regulate the neurotransmitter synthesis by the implanted cells. Dosages necessary to achieve the desired effect will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved. The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition.

Modalities of Treatment/Prophylaxis

In some embodiments, the subject receiving adherent stromal cell treatment has early-onset PE (about 20 to about 34 weeks of gestation). In cases of early onset of PE, the prognosis includes rapid progression, multiple complications, and poor perinatal outcome. Moreover, for gestational age of less than 24 weeks of gestation, expectant treatment is associated with high maternal morbidity and minimal perinatal benefit [15, 16]. In some embodiments, the subject receives cell treatment immediately following diagnosis.

In further embodiments, the subject receiving adherent stromal cell treatment has late-onset PE. In cases of late onset PE (about 34 to 38 weeks or more of gestation), the prognosis is usually good and expectant management is possible. Treatment with the cell therapy described herein can alleviate symptoms, thereby potentially reducing complications as well as reducing expensive hospital stay time and long term complications.

In some embodiments, the adherent stromal cells, such as adherent stromal cells from placental or adipose tissue, are used in methods of prophylactic treatment. Prophylactic treatment may be given to the subject at any point of gestation or prior to gestation. For example, prophylactic treatment may be given to the subject in the first trimester, second trimester, or third trimester. In some embodiments, the subject receives prophylactic treatment at about 12 to about 28 weeks of gestation, or from about 6 to about 38 or more weeks of gestation, or at any week of gestation, including from the first week of gestation until delivery. In some embodiments of prophylactic treatment, the subject receives treatment at about 16 to about 20 weeks of gestation. In some embodiments, the subject is genetically predisposed to PE. In further embodiments, the subject has a PE history in past pregnancies. In some embodiments, a potential case of PE is detected in a subject using biomarkers, including placental growth factor (PlGF) and soluble fms-like tyrosine kinase-1 (sFlt-1). The etiology of PE is associated with early developmental processes of placental development, which are angiogenic/tissue modulatory in nature. Accordingly, in some embodiments, the cell therapy described herein (e.g., PLX therapy) may prevent PE from appearing in the first place. PLX therapy exhibits maternal and fetal safety, and accordingly, embodiments encompass prophylactic PLX therapy for at-risk populations.

In some embodiments, adherent stromal cells are administered to a subject having one or more risk factors for PE. The corollary is that any factor that would increase the maternal systemic inflammatory response to pregnancy would predispose the mother to preeclampsia regardless of its origin. Risk factors for PE include the following: maternal obesity and associated inflammation, risk factors for cardiovascular diseases such as chronic hypertension, pre-existing diabetes mellitus, hyperlipidemia, and advanced maternal age [19]. These women are more likely to be overweight, have higher lipid levels, higher blood pressure, insulin resistance, and are more likely to have a thrombophilia, compared with women who go on to have a normotensive pregnancy [20].

Women with higher blood pressures in early pregnancy appear to be more sensitive to the circulating anti-angiogenic factors sFlt-1 and sEng, and as a consequence, they develop preeclampsia at lower concentrations of these factors [21]. Although these risk factors are not highly predictive when used on their own, they assist in the identification of women at risk and can improve maternal outcome and possibly perinatal outcome as well [22].

Taken together, these observations support the notion that pre-existing maternal sub-clinical endothelial dysfunction, as recognized by chronic hypertension, makes a woman more vulnerable to poor placentation and more sensitive to the consequences of placental dysfunction. A woman's pre-pregnancy metabolic and endothelial health therefore affects her vulnerability to preeclampsia, which in turn is a clinical manifestation of her risk of future metabolic and cardiovascular disease in later life.

Other risk factors include preeclampsia in a prior pregnancy, especially in cases of early-onset PE; preeclampsia in a first-degree relative (increasing a woman's risk of severe preeclampsia two- to fourfold); specific medical conditions, including diabetes mellitus, renal disease, metabolic syndrome, and a hypercoaguable state; very young maternal age; advanced maternal age; increased placental mass; multifetal gestation; a hydatidiform mole; prenatal paternity by a man who fathered a prior preclamptic pregnancy with a prior partner; a reduced serum concentration of placental growth factor (PlGF); an increased serum concentration of soluble fms-like tyrosine kinase-1 (sFlt-1); an increased ratio of sFlt-1:PlGF; and an increased serum concentration of soluble endoglin.

In some embodiments, the subject is administered adherent stromal cells with a dosage of about 150 to about 300 million cells. In some embodiments, subsequent doses are lower in cell number. Doses may be administered at multiple time points and/or at variable intervals. In some embodiments, the schedule of administration and/or dosing is determined in consultation with a gynecologist.

EXAMPLES

Example 1: PLX, Adipose Adherent Stromal Cell, and Bone Marrow Adherent Stromal Cell Treatment Reduces Blood Pressure During Pregnancy in Preeclampsia Mice RNA, in either dsRNA or ssRNA forms, plays a primary role in the development of PE, as RNA receptor activation during pregnancy causes inflammation, endothelial and placental dysfunction, and hypertension in rats, mice, and humans [23-25]. DsRNA and ssRNA expressed by viruses as well as released from injured/dying cells activate highly conserved, specific RNA receptors (Toll-like Receptor 3 [TLR3] for dsRNA; Toll-like Receptor 7 [TLR7] for ssRNA) and lead to a pro-inflammatory immune response. Toll-like receptors, like other innate immune system receptors, are highly conserved and respond to pathogen-associated molecular patterns (PAMPs) and endogenous ligands released from dying or injured cells by initiating pro-inflammatory signaling pathways and activating the adaptive immune system. Activation of TLR3 by the agonist polyinosinic-polycytidylic acid (poly(I:C)) in rats and mice causes systemic inflammation in both pregnant and non-pregnant animals, and it causes hypertension, proteinuria, and endothelial dysfunction in pregnant animals [23-25]. TLR7 activation during pregnancy in mice also causes pregnancy-dependent hypertension, endothelial dysfunction, splenomegaly, and an increased incidence of fetal demise [25]. Given this symptomatic similarity to PE in humans, these results suggest that excessive TLR3 and TLR7 activation initiates the symptoms of PE in humans [25] and show that TLR3 and TLR7 activation in mice is a useful model for the study of PE in humans.

Pregnant C57Bl/6J mice were injected intraperitoneally with either the Toll-like Receptor 3 (TLR3) agonist polyinosinic-polycytidylic acid (poly(I:C)) (PPIC mice), the Toll-like Receptor 7 (TLR7) agonist R837 (imiquimod) (PR mice), or saline vehicle (P mice) on days 13, 15, and 17 of pregnancy. On gestational day 14, PLX cells were prepared and processed into 25 □l of plasmaLyte A (PLA) containing 0.5 million PLX cells. Following tail-cuff systolic blood pressure measurements, two P, two PPIC, and two PR mice received either PLA vehicle injections or injections of PLX cells. One P, one PPIC, and one PR mouse were each given two separate 25 □l injections of PLA into the muscle of the right leg while under brief anesthesia (isoflurane). The remaining P, PPIC, and PR mice each received two separate 25 □l injections of PLX cells ($10^6$ cells total) in the muscle of the right leg while under brief anesthesia (isoflurane). The mice recovered quickly and showed no ill effects from the anesthesia or the injections. The six mice, housed in groups of two, were placed back into their standard housing conditions with food and water ad libitum. Systolic blood pressures were taken in the afternoons of gestational days 15, 16, and 17 and were performed prior to TLR injections on days 15 and 17 by two investigators blinded to the identity of each mouse (PLA vs. PLX).

PPIC and PR mice exhibited significantly increased systolic blood pressure by gestational day 14 which remained elevated through day 17 (FIG. 1; P=pregnant, PPIC=pregnant+poly (I:C), and PR=pregnant+R837; n is shown in parentheses; data are presented as mean+/−SEM; asterisk indicates p-value of <0.05 vs. P+PLA). All mice receiving intramuscular injections of PLA vehicle had no change in blood pressure (solid black symbols in FIG. 1). However, PPIC and PR mice that received PLX cells had a progressive, significant decrease in blood pressure which returned to P levels by day 17 (black-outlined symbols in FIG. 1). Additionally, PLX cell treatment had no effect on blood pressure in P mice.

A similar experiment was performed using adherent stromal cells derived from bone marrow or adipose tissue. The experiment was performed as described above, with $10^6$ cells administered by i.m. injection on day 14 to PPIC mice. The results are shown in Table 1, which shows a decrease in SBP values at days 14-17 post-administration. For each of the cell types administered (i.e., bone marrow or adipose), the results demonstrate a decrease in elevated SBF from day 14 to day 17 of gestation following cell administration.

TABLE 1

|  | D14 | D15 | D16 | D17 |
|---|---|---|---|---|
| Bone Marrow | 141 | 142 | 144 | 116 |
|  | 138 | 142 | 140 | 112 |
|  | 153 | 154 | 155 | 123 |
| Adipose | 135 | 142 | 140 | 94 |
|  | 135 | 160 | 159 | 117 |
|  | 139 | 144 | 146 | 109 |

Figure 2:
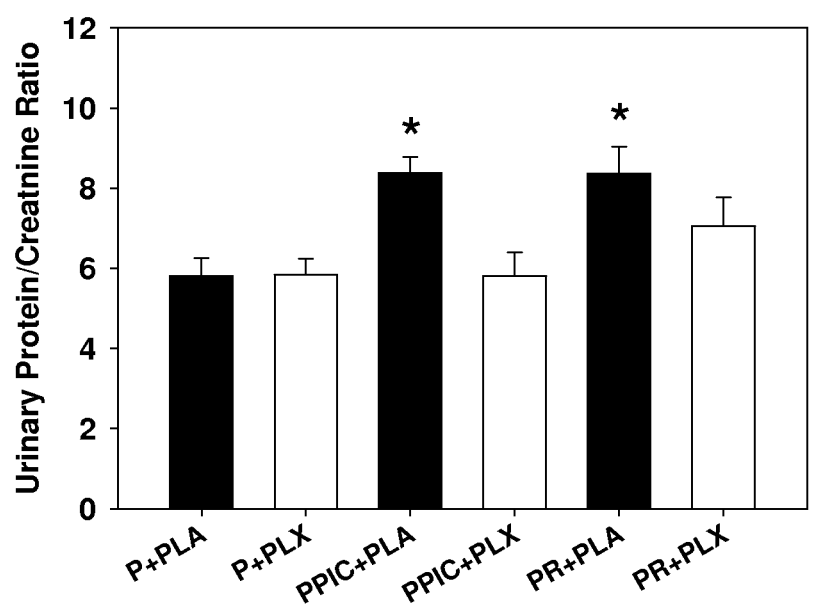
FIG. 2. P, PPIC, and PR mice were treated with either PLA vehicle or PLX cells ($10^6$ cells total) by i.m. injections in the right leg on gestational day 14. Protein and creatinine levels were assayed using urine collected on day 18 during euthanization. N=4 for P+PLA and P+PLX, N=6 for the other 4 groups. Data are presented as mean+SEM. *$p<0.05$ vs. P+PLA.

Example 2: PLX, Adipose Adherent Stromal Cell, and Bone Marrow Adherent Stromal Cell Treatment Reduces Proteinuria During Pregnancy in Preeclampsia Mice TLR-induced PE mice exhibit proteinuria, a clinical determinant of PE in humans. PE was induced in pregnant C57Bl/6J mice and the mice were treated with PLX cells or PLA vehicle as described in Example 1. Mice were euthanized on gestational day 18, at which time urine was collected and urinary protein was measured. The measured protein values were normalized to urinary creatinine levels. PLX cell treatment on day 14 normalized urinary protein/creatinine ratios in PPIC and PR mice, while it had no effect in P mice (FIG. 2; P=pregnant, PPIC=pregnant+poly (I:C), and PR=pregnant+R837; n=4 for P+PLA and P+PLX, n=6 for the other 4 groups; data are presented as mean+SEM; asterisk indicates p-value of <0.05 vs. P+PLA). Thus, PLX cell treatment ameliorated proteinuria in PPIC and PR mice.

A similar experiment was performed using adherent stromal cells derived from bone marrow or adipose tissue. The experiment was performed as described above, with $10^6$ cells administered by i.m. injection on day 14 to PPIC mice. The results are shown in Table 2, which shows that BM and Adipose derived adherent cell treatment on day 14 reduced urinary protein/creatinine ratios in PPIC mice, Thus, bone marrow adherent stromal cell and adipose adherent stromal cell treatment ameliorated proteinuria in PPIC mice.

TABLE 2

|  | PPIC + PLA | PPIC + Adipose | PPIC + BM |
|---|---|---|---|
| Mean | 5.68 | 3.73 | 2.42 |
| sem | 0.17 | N/A | 0.29 |

Figure 3:
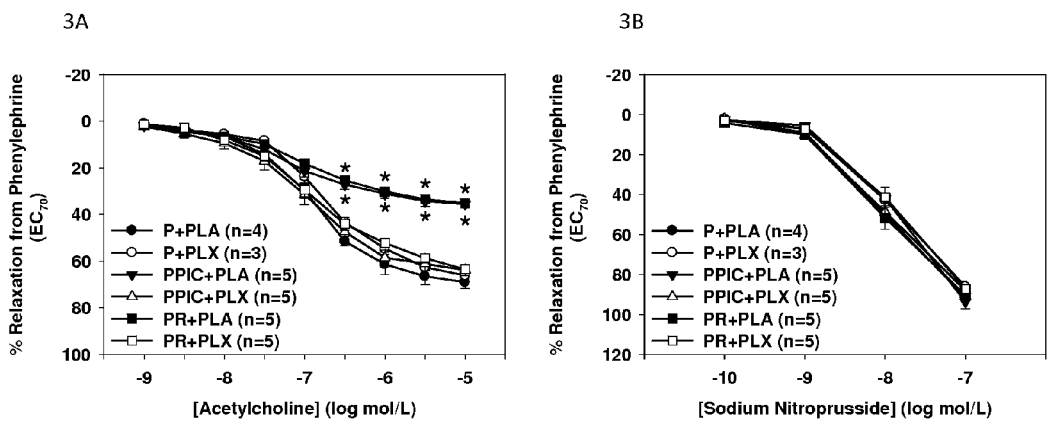
FIGS. 3A and 3B. P, PPIC, and PR mice were treated with either PLA vehicle or PLX cells ($10^6$ cells total) by i.m. injections in the right leg on gestational day 14. Aortas were collected on day 18 during euthanization and mounted on pins in a DMT 210 myograph containing physiological salt solution heated to 37° C. and bubbled with 95% O2/5% CO2. PPIC and PR mice exhibit endothelial dysfunction (decreased acetylcholine-induced relaxation (FIG. 3A), normal sodium nitroprusside-induced relaxation FIG. 3B)) which was ameliorated by PLX cell treatment. N is provided in parentheses. Data are presented as mean+SEM. *$p<0.05$ vs. P+PLA.

Example 3: PLX Cell Treatment Mitigates Endothelial Dysfunction During Pregnancy in Preeclampsia Mice Humans with PE characteristically exhibit endothelial dysfunction, or the decreased ability of blood vessels to relax in response to vasodilator stimuli. TLR-induced PE mice also exhibit endothelial dysfunction, which is evidenced by a significant decrease in relaxation responses to the endothelium-dependent dilator acetylcholine but normal relaxation responses to the endothelium-dependent dilator sodium nitroprusside. PE was induced in pregnant C57Bl/6J mice and the mice were treated with PLX cells or PLA vehicle as described in Example 1. Aortas were collected on gestational day 18 after euthanasia and were mounted on pins in a DMT 210 myograph containing physiological salt solution heated to 37° C. and bubbled with 95% $O_2$/5% $CO_2$. PLX cell treatment restored aortic endothelium-dependent relaxation responses to acetylcholine in PPIC and PR mice (FIG. 3A) while having no effect on endothelium-independent relaxation responses to sodium nitroprusside (FIG. 3B; for FIG. 3: P=pregnant, PPIC=pregnant+poly (I:C), and PR=pregnant+R837; n is provided in parentheses; data are presented as mean+SEM; asterisk indicates p-value of <0.05 vs. P+PLA). Thus, PLX cell treatment of PPIC and PR mice increased acetylcholine-mediated aortic relaxation responses, indicating amelioration of endothelial dysfunction in the PE mice.

Example 4: PLX Cell Treatment is not Detrimental to Fetuses in Pregnant PE Mice

Figure 4:
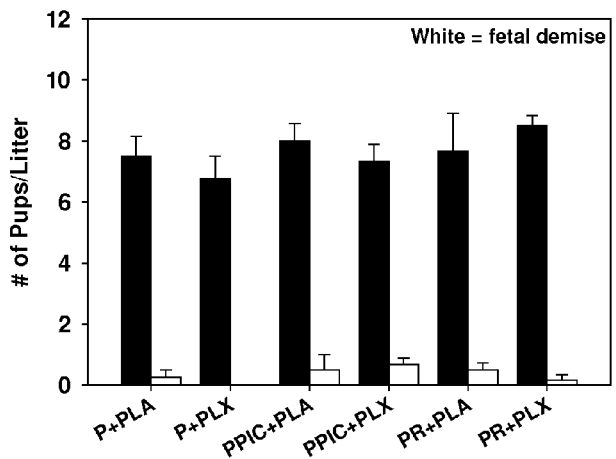
FIG. 4. P, PPIC, and PR mice were treated with either PLA vehicle or PLX cells ($10^6$ cells total) by i.m. injections in the right leg on gestational day 14. Pup number per litter and fetal demise per litter were assessed by 2 investigators on day 18 during euthanization. There were no significant differences in the number of pups or fetal demise per litter. N=4 for P+PLA and P+PLX, N=6 for the other 4 groups. Data are presented as mean+SEM.

The effects of PLX cell treatment on fetal development was assessed by determining the number of pups per litter from PLX-treated PE mice and the incidence of fetal demise in each litter. PE was induced in pregnant C57Bl/6J mice and the mice were treated with PLX cells or PLA vehicle as described in Example 1. Pup number per litter and incidence of fetal demise per litter were assessed on day 18 during euthanasia by two investigators blinded to the identity of each mouse. No significant differences were apparent in the number of pups per litter and in the incidence of fetal demise in any of the six groups of mice (FIG. 4; P=pregnant, PPIC=pregnant+poly (I:C), and PR=pregnant+R837; n=4 for P+PLA and P+PLX; n=6 for the other four groups; data are presented as mean+SEM). This indicates that PLX cell treatment does not harm the fetuses.

Example 5: PLX Cells are not Immunogenic in Pregnant Mice

Figure 5:
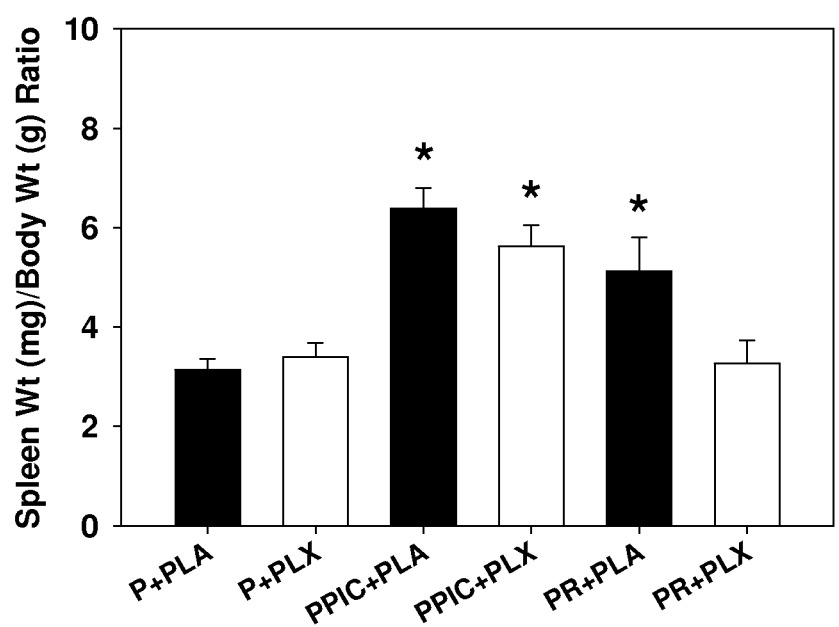
FIG. 5. P, PPIC, and PR mice were treated with either PLA vehicle or PLX cells ($10^6$ cells total) by i.m. injections in the right leg on gestational day 14. Spleen weight and body weight were measured on day 18 during euthanization. PLX cells ameliorated the splenomegaly in PR mice but not PPIC mice. N=6 for the other 4 groups. Data are presented as mean+SEM. *$p<0.05$ vs. P+PLA.

Women with PE typically experience splenomegaly, or enlargement of the spleen, which represents an active immune response. To assess the state of the immune system during pregnancy in PLX cell-treated PE mice, PE was induced in pregnant C57Bl/6J mice and the mice were treated with PLX cells or PLA vehicle as described in Example 1. On gestational day 18, mice were euthanized, and spleen weight was measured and normalized to body weight. PLX cell treatment did not increase spleen size in P mice, demonstrating the lack of immunogenicity of PLX cells (FIG. 5). PPIC and PR mice exhibit splenomegaly (FIG. 5). PLX cell treatment normalized the spleen weight-to-body weight ratio in the PE mice injected with R837 (PR mice), but the treatment did not dramatically reduce the spleen weight-to-body weight ratio in the poly (I:C)-injected (PPIC) mice (FIG. 5; P=pregnant, PPIC=pregnant+poly (I:C), and PR=pregnant+R837; n=4 for P+PLA and P+PLX, n=6 for the other four groups; data are presented as mean+SEM; asterisk indicates p-value of <0.05 vs. P+PLA).

Figure 6:
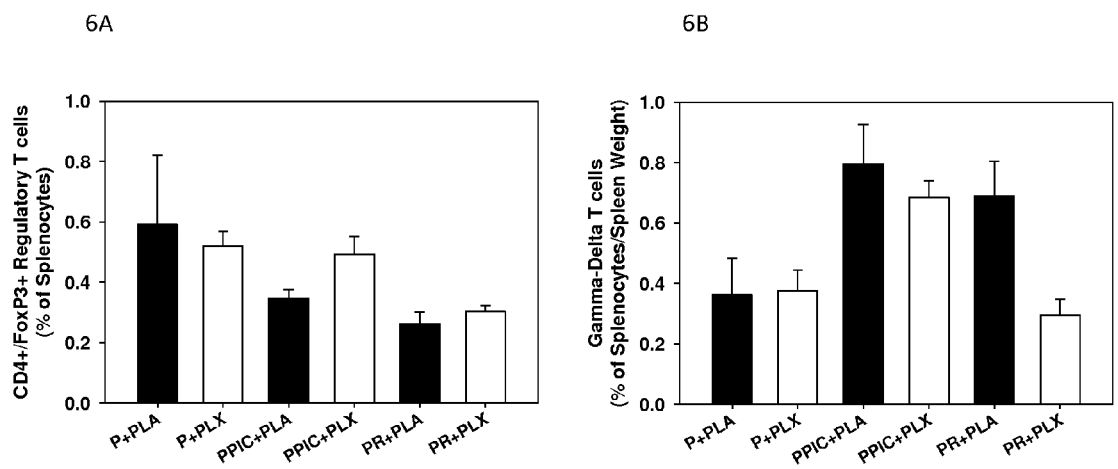
FIGS. 6A and 6B. P, PPIC, and PR mice were treated with either PLA vehicle or PLX cells ($10^6$ cells total) by i.m. injections in the right leg on gestational day 14 Immune cell subsets were measured by flow cytometry on day 18 following euthanization. PLX cells ameliorated the decrease in regulatory T cells in PPIC mice but not PR mice (FIG. 6A), while decreasing γδ T cells in PR mice but not PPIC mice (FIG. 6B). N=2-4 for all groups. Data are presented as mean+SEM.

Example 6: Changes in Immune Cell Levels with PE Development and PLX Cell Treatment We also examined whether changes in immune cell subsets were associated with the development of PE and the reduction in PE symptoms mediated by PLX cell treatment. PE was induced in pregnant C57Bl/6J mice and the mice were treated with PLX cells or PLA vehicle as described in Example 1. On gestational day 18, mice were euthanized, and levels of the anti-inflammatory, tolerogenic immune cells regulatory T cells ($T_{regs}$; CD4+/FoxP3+) and the pro-inflammatory immune cells γδ T cells (CD3+/γδ+) were determined by flow cytometry. As FIG. 6A demonstrates, splenic levels of $T_{regs}$ were decreased in PPIC and PR mice relative to P mice. PLX cell treatment restored levels of $T_{regs}$ in PPIC mice, but not in PR mice (FIG. 6A). Additionally, splenic levels of γδ T cells, when normalized to spleen weight, were elevated in PPIC and PR mice (FIG. 6B). PLX cell treatment lowered γδ T cell levels to normal in PR mice, but not in PPIC mice (FIG. 6B). (For FIG. 6: P=pregnant, PPIC=pregnant+poly (I:C), and PR=pregnant+R837; n=2-4 for all groups; data are presented as mean+SEM.)

Figure 7:
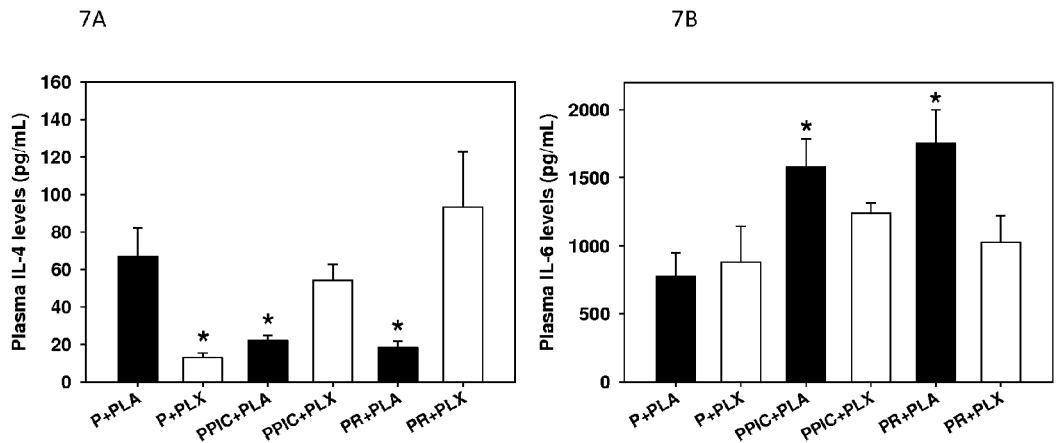
FIGS. 7A and 7B. P, PPIC, and PR mice were treated with either PLA vehicle or PLX cells ($10^6$ cells total) by i.m. injections in the right leg on gestational day 14. Whole blood was collected on day 18 during euthanization and plasma was isolated and assayed for IL-4 and IL-6 by ELISA. PPIC and PR mice exhibit significantly reduced levels of IL-4 (FIG. 7A) and increased levels of IL-6 (FIG. 7B) which were both normalized by PLX cell treatment. Data are presented as mean+SEM. *$p<0.05$ vs. P+PLA by one-way ANOVA.

Example 7: PLX Restore Plasma Levels of IL-4 During Pregnancy in Preeclampsia Mice Consistent with the PLX cell-induced decrease in splenomegaly and γδ T cells, we observed a restoration of plasma levels of the anti-inflammatory cytokine IL-4, which is important for normal pregnancy, and normalization of plasma levels of the pro-inflammatory cytokine IL-6 in PPIC and PR mice (FIG. 7). P, PPIC, and PR mice were treated with either PLA vehicle or PLX cells ($10^6$ cells total) by i.m. injections in the right leg on gestational day 14. Whole blood was collected on day 18 during euthanization and plasma was isolated and assayed for IL-4 and IL-6 by ELISA. PPIC and PR mice exhibit significantly reduced levels of IL-4 and increased levels of IL-6 which were both normalized by PLX cell treatment. Pregnant, PPIC=pregnant+poly I:C (TLR3 agonist), and PR=pregnant+R837 (TLR7 agonist). Data are presented as mean+SEM. *$p<0.05$ vs. P+PLA by one-way ANOVA.

These data taken together suggest that PLX cell treatment reduces inflammation which may mediate the reduction of PE symptoms in PPIC and PR mice.

Figure 8:
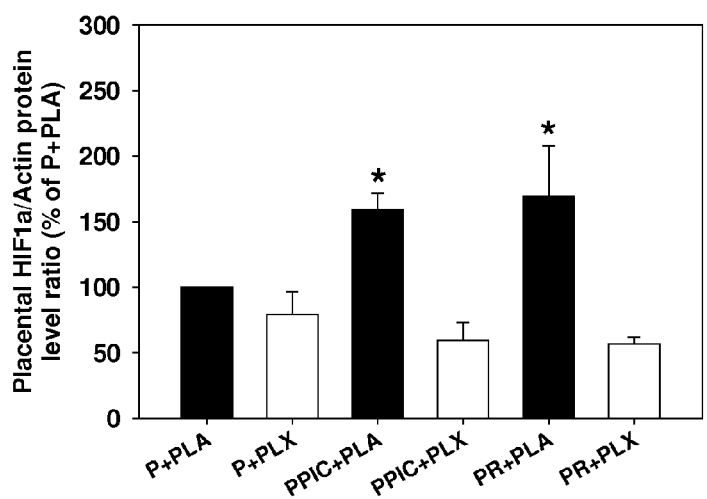
FIG. 8. P, PPIC, and PR mice were treated with either PLA vehicle or PLX cells ($10^6$ cells total) by i.m. injections in the right leg on gestational day 14. HIF1_protein levels were measured by immunoblot in placentas obtained on day 18 following euthanization and normalized to actin levels. PLX cells decreased HIF1_protein levels in PPIC and PR mice. Data are presented as mean+SEM as a % of P+PLA. *$p<0.05$ vs. P+PLA by one-way ANOVA.

Example 8: PLX Cells Decreased HIF1α Protein During Pregnancy in Preeclampsia Mice Next, we examined placental levels of the hypoxia marker HIF1α by immunoblot to determine if placental injury occurred in PPIC and PR mice and whether PLX cell treatment had any effect. HIF1α protein levels were increased significantly in placentas from PPIC and PR mice and this was prevented by PLX cell treatment (FIG. 8).

P, PPIC, and PR mice were treated with either PLA vehicle or PLX cells ($10^6$ cells total) by i.m. injections in the right leg on gestational day 14. HIF1α protein levels were measured by immunoblot in placentas obtained on day 18 following euthanization and normalized to actin levels. PLX cells decreased HIF1α protein levels in PPIC and PR mice. P=pregnant, PPIC=pregnant+poly I:C (TLR3 agonist), and PR=pregnant+R837 (TLR7 agonist). Data are presented as mean+SEM as a % of P+PLA. *$p<0.05$ vs. P+PLA by one-way ANOVA.

Figure 9:
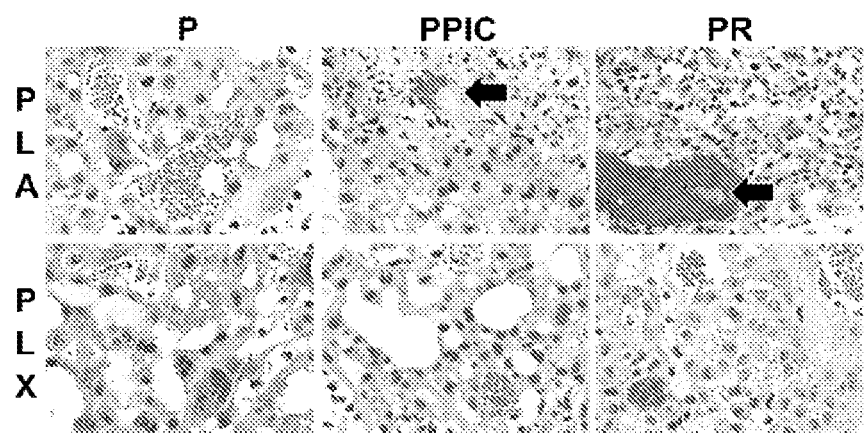
FIG. 9. P, PPIC, and PR mice were treated with either PLA vehicle or PLX cells (106 cells total) by i.m. injections in the right leg on gestational day 14. H&E staining was performed on placentas obtained on day 18 following euthanization. Images provided are at 10× magnification. PLX cells decreased fibrin deposition (black arrows) around placental blood vessels in PPIC and PR mice. Pregnant, PPIC=pregnant (TLR3 agonist), and PR=pregnant+R837 (TLR7 agonist).

Example 9: PLX Cells Decreased Fibrin Deposition Around Placental Blood Vessels During Pregnancy in Preeclampsia Mice We also examined placental injury by histology using H&E staining and light microscopy. We observed eosin-positive cells, which depicts fibrin deposition, in cells around the placental vasculature of PPIC and PR mice, and this was not observed in placentas from PLX-treated mice (FIG. 9).

P, PPIC, and PR mice were treated with either PLA vehicle or PLX cells ($10^6$ cells total) by i.m. injections in the right leg on gestational day 14. H&E staining was performed on placentas obtained on day 18 following euthanization. Images provided are at 10× magnification. PLX cells decreased fibrin deposition (black arrows) around placental blood vessels in PPIC and PR mice. P=pregnant, PPIC=pregnant+poly I:C (TLR3 agonist), and PR=pregnant+R837 (TLR7 agonist).

Together, these data demonstrate that PLX cell treatment at gestational day 14 is able to normalize systolic blood pressure, proteinuria, and endothelial function while having no detrimental fetal effects in mice. While the mechanisms remain to be determined precisely, these preliminary data suggest that PLX cell treatment exerts beneficial effects by reducing inflammation, placental hypoxia, and placental injury and demonstrate that PLX cells may be a potential novel therapeutic for the treatment of PE.

It is to be understood that the foregoing description is exemplary and explanatory only and is not restrictive of the invention as claimed. Other embodiments of the invention will be apparent to those skilled in the art from consideration of the specification and practice of the invention disclosed herein. It is intended that the specification and examples be considered as exemplary only.

REFERENCES

1. Young, B. C., R. J. Levine, and S. A. Karumanchi, *Pathogenesis of preeclampsia*. Annu Rev Pathol, 2010. 5: p. 173-92.
2. Khan, K. S., et al., *WHO analysis of causes of maternal death: a systematic review*. Lancet, 2006. 367(9516): p. 1066-74.
3. Robbins, S. L., V. Kumar, and R. S. Cotran, *Robbins and Cotran pathologic basis of disease*. 8th ed. 2010, Philadelphia, Pa.: Saunders/Elsevier. xiv, 1450 p.
4. Lunell, N. O., et al., *Uteroplacental blood flow in pregnancy induced hypertension*. Scand J Clin Lab Invest Suppl, 1984. 169: p. 28-35.
5. Cross, S. N., et al., *Bevacizumab-mediated interference with VEGF signaling is sufficient to induce a preeclampsia-like syndrome in nonpregnant women*. Rev Obstet Gynecol, 2012. 5(1): p. 2-8.
6. Ryznar, V., J. Erban, and J. Pohanka, *Pregnancy-induced hypertension and its influence on uteroplacental blood flow*. Acta Univ Palacki Olomuc Fac Med, 1988. 119: p. 361-5.
7. Woods, A. K., et al., *Adenoviral delivery of VEGF121 early in pregnancy prevents spontaneous development of preeclampsia in BPH/5 mice*. Hypertension, 2011. 57(1): p. 94-102.
8. Gammill, H. S., et al., *Pregnancy, microchimerism, and the maternal grandmother*. PLoS One, 2011. 6(8): p. e24101.
9. McCarthy, F. P., et al., *Animal models of preeclampsia; uses and limitations*. Placenta, 2011. 32(6): p. 413-9.
10. Khalil, R. A. and J. P. Granger, *Vascular mechanisms of increased arterial pressure in preeclampsia: lessons from animal models*. Am J Physiol Regul Integr Comp Physiol, 2002. 283(1): p. R29-45.
11. Podjarny, E., G. Losonczy, and C. Baylis, *Animal models of preeclampsia*. Semin Nephrol, 2004. 24(6): p. 596-606.
12. Chang, E. Y., et al., *The use of N-acetylcysteine for the prevention of hypertension in the reduced uterine perfusion pressure model for preeclampsia in Sprague-Dawley rats*. Am J Obstet Gynecol, 2005. 193(3 Pt 2): p. 952-6.
13. Sharkey, L. C., et al., *Spontaneous pregnancy-induced hypertension and intrauterine growth restriction in rats*. Am J Hypertens, 2001. 14(10): p. 1058-66.
14. Ishida, J., et al., *Pregnancy-associated homeostasis and dysregulation: lessons from genetically modified animal models*. J Biochem, 2011. 150(1): p. 5-14.
15. Sibai, B. M. and J. R. Barton, *Expectant management of severe preeclampsia remote from term: patient selection, treatment, and delivery indications*. Am J Obstet Gynecol, 2007. 196(6): p. 514 e1-9.
16. Gong, Y. H., et al., *Outcome and risk factors of early onset severe preeclampsia*. Chin Med J (Engl), 2012. 125(14): p. 2623-7.
17. Levine, R. J., et al., *Circulating angiogenic factors and the risk of preeclampsia*. N Engl J Med, 2004. 350(7): p. 672-83.
18. Levine, R. J., et al., *Soluble endoglin and other circulating antiangiogenic factors in preeclampsia*. N Engl J Med, 2006. 355(10): p. 992-1005.
19. Magnussen E. B., et al., *Prepregnancy cardiovascular risk factors as predictors of pre-eclampsia: population based cohort study*. BMJ 2007; 335:978.
20. Williams D. J., *Pregnancy: a stress test for life*. Curr Opin Obstet Gynecol 2003; 15:465-71.
21. Noori M. et al., *Prospective study of placental angiogenic factors and maternal vascular function before and after preeclampsia and gestational hypertension*. Circulation 2010; 122:478-87.
22. Chandiramani M., Waugh J. J. S., and Shennan A. H. *Management of hypertension and pre-eclampsia in pregnancy*. Trends Urol Gynaecol Sex Health 2007; 12:23-28.
23. Tinsley J H, Chiasson V L, Mahajan A, Young K J, Mitchell B M. *Toll-like receptor 3 activation during pregnancy elicits preeclampsia-like symptoms in rats*. Am J Hypertens. 2009; 22:1314-1319.
24. Chatterjee P, Chiasson V L, Kopriva S E, Young K J, Chatterjee V, Jones K A, Mitchell B M. *Interleukin 10 deficiency exacerbates toll-like receptor 3-induced preeclampsia-like symptoms in mice*. Hypertension. 2011; 58:489-496.
25. Chatterjee P, Weaver L E, Doersch K M, Kopriva S E, Chiasson V L, Allen S J, Narayanan A M, Young K J, Jones K A, Kuehl T J, Mitchell B M. *Placental toll-like receptor 3 and toll-like receptor 7/8 activation contributes to preeclampsia in humans and mice*. PLoS One. 2012; 7:e41884.

What is claimed is:

1. A method of reducing blood pressure in a subject with preeclampsia or eclampsia, comprising administering to the subject an effective amount of adherent stromal cells derived from a placenta, thereby reducing the blood pressure.
2. The method of claim 1, wherein the subject has early-onset preeclampsia.
3. The method of claim 2, wherein the subject is at a period of gestation of from about 20 weeks to about 34 weeks.
4. The method of claim 1, wherein the subject has late-onset preeclampsia.
5. The method of claim 1, wherein the adherent stromal cells are administered intramuscularly.
6. The method of claim 1, wherein the adherent stromal cells are allogeneic to said subject and said subject's fetus.
7. A method of treating hypertension in a subject with preeclampsia or eclampsia, comprising administering to the subject an effective amount of adherent stromal cells derived from a placenta, thereby treating the hypertension.
8. The method of claim 7, wherein the subject has early-onset preeclampsia.
9. The method of claim 8, wherein the subject is at a period of gestation of from about 20 weeks to about 34 weeks.
10. The method of claim 7, wherein the subject has late-onset preeclampsia.
11. The method of claim 7, wherein the adherent stromal cells are administered intramuscularly.
12. The method of claim 7, wherein the adherent stromal cells are allogeneic to said subject and said subject's fetus.
13. The method of claim 7, wherein the subject is in first trimester, second trimester, or third trimester.
14. The method of claim 7, wherein the subject is at a period of gestation of from about 6 weeks to about 38 weeks.
15. A method of reducing proteinuria in a subject with preeclampsia or eclampsia, comprising administering to the subject an effective amount of adherent stromal cells derived from a placenta, thereby reducing the proteinuria.
16. The method of claim 15, wherein the subject has early-onset preeclampsia.
17. The method of claim 16, wherein the subject is at a period of gestation of from about 20 weeks to about 34 weeks.

18. The method of claim 15, wherein the subject has late-onset preeclampsia.

19. The method of claim 15, wherein the adherent stromal cells are administered intramuscularly.

20. The method of claim 15, wherein the adherent stromal cells are allogeneic to said subject and said subject's fetus.

* * * * *